United States Patent [19]

Acres et al.

[11] 4,298,597

[45] Nov. 3, 1981

[54] **VACCINE FOR DIARRHEA CAUSED BY *E. COLI***

[75] Inventors: Stephen D. Acres; Robert A. Kapitany, both of Saskatoon, Canada

[73] Assignee: University of Saskatchewan, Saskatoon, Canada

[21] Appl. No.: 71,994

[22] Filed: Sep. 4, 1979

[51] Int. Cl.$^3$ .................. A61K 39/108; A61K 39/116
[52] U.S. Cl. ........................................ 424/92; 424/88
[58] Field of Search ...................... 424/92, 87, 88, 180

[56] References Cited

U.S. PATENT DOCUMENTS 3,907,987  9/1975  Wilson .................................. 424/92

OTHER PUBLICATIONS

Sojka, W. et al., J. Med. Microbiol., vol. 11, pp. 493-498 (1978).
Myers, L., The American Journal of Veterinary Research, vol. 39, No. 5, pp. 761-769, (1978).
Acres, S. et al., Infection and Immunity, vol. 25, pp. 121-126, (1979).
Dobrescu, L. et al., Zbl. Vet. Med. B, vol. 23, pp. 79-88 (1976).
Myers, L., The American Journal of Veterinary Research, vol. 34, pp. 29-33 (1973).
Nagy, B., Infection and Immunity, vol. 27, No. 1, pp. 21-24 (1980).
Morris, J. A. et al., J. of General Microbiology, vol. 99, pp. 353-357 (1977).
Myers, L., The American Journal of Veterinary Research, vol. 37, No. 7, pp. 831-834 (1976).
Nagy, B. et al., Infection and Immunity, vol. 21, pp. 269-274 (1978).
Nagy et al., Research in Veterinary Science, vol. 24, pp. 39-45, (1978).
Newman, F. et al., Infection and Immunity, vol. 8, No. 4, pp. 540-543 (1973).
Varga et al., Acta Veterinaria Academiae Scientiarum Hungaricae, Tomas 26(1) pp. 49-54 (1976).
Acres, S., Abstract of Thesis, pp. 288-300 (1976).
Myers, L., Second International Symposium on Neonatal Diarrhea, pp. 427-442 (1979).
Acres et al., Second International Symposium on Neonatal Diarrhea, pp. 443-456 (1979).
Ecopig, Smith Kline Laboratories, 1977.
Dobrescu et al., Proceedings Int. Pig Vet. Soc., 1976 Cong., Ames, Iowa.
Dobrescu et al., Zbl. Vet. Med. B., vol. 20, pp. 222-229 (1973).
Smith, H. et al., J. Path. Bact., vol. 93, pp. 531-543 (1967).
Smith, H. et al., J. Med. Microbiol., vol. 3, pp. 387-401 (1970).

*Primary Examiner*—Delbert R. Phillips
*Assistant Examiner*—Blondel Hazel
*Attorney, Agent, or Firm*—Depaoli & O'Brien

[57] ABSTRACT

A relatively safe and effective vaccine for coliform diarrhea and related infections is prepared from semipurified K99 and other concentrated subcellular antigens and organelles of selected *E. coli* strains. For this purpose broth cultures of *E. coli* bacteria are mechanically sheared or sonicated to disrupt the bacterial cells, then centrifuged and the supernatent containing subcellular particles and components is concentrated by ultrafiltration and sterilized by the addition of a preservative and/or stabilizer.

21 Claims, No Drawings

VACCINE FOR DIARRHEA CAUSED BY E. COLI

This invention deals with the subcellular vaccines from the bacterium *Escherichia coli* (*E. coli*), their preparation and use. A subunit vaccine against enterotoxigenic colibacillosis is prepared from selected strains.

Enterotoxigenic colibacillosis occurs in cattle, sheep and swine. In calves it occurs primarily during the first 5 days after birth, probably because calves become resistant to the bacterium within a few days following birth. This resistance does not appear to be antibody dependent and is probably physiological in nature; i.e. a change in the intraluminal environment of the small intestine or in the nature of the cells lining the small intestine. The *E. coli* which are capable of causing the disease appear to possess at least 2 attributes of virulence. Firstly, they have pili and/or colonizing factors on their surface which allow them to attach to the mucosa of the small intestine. In bovine enterotoxigenic *E. coli* (ETEC), one of the important factors is known as the K99 antigen, which appears as a layer of fine filaments or hair-like structures on the surface of the bacteria and whose function it is to attach the bacteria to the surface of the cells lining the small intestine. Other factors, eg. polysaccharide K antigens, have recently been implicated in the colonization process. Secondly, the bacteria produce enterotoxins which cause the intestine to secrete large volumes of fluid.

Previous work in pigs showed that vaccination of pregnant sows with colonizing factors of porcine ETEC prevented diarrhea and death in suckling piglets. (L. K. Nagy et al., Res. Vet. Sci. (1978) 24: 39–45; B. Nagy et al., Infect. Immun. (1978) 21: 269–274) Therefore, pregnant cows were immunized with the colonizing factor of bovine ETEC, ie. K99 antigen, as well as with other subcellular particles such as polysaccharide K antigens, lipopolysaccharide O antigens and heat-stable enterotoxins to stimulate the formation of colostral antibodies, in particular, anti-K99 antibody, which, in turn, prevent neonatal diarrhea in suckling calves.

According to this invention, a relatively safe and effective vaccine for enterotoxigenic colibacillosis and related infections is prepared from semipurified K99 and other concentrated subcellular antigens and organelles of selected *E. coli* strains. For this purpose, broth cultures of *E. coli* bacteria are mechanically sheared or sonicated to disrupt the bacterial cells, then centrifuged and the supernatent containing subcellular particles and components is concentrated by ultrafiltration, sterilized, and a preservative and/or stabilizer is added.

The vaccine normally contains the entire broth culture constituents, including metabolic end products and extracellular proteins, but excluding intact bacterial cells. Ultrafiltration increased the concentration of the subcellular components.

Vaccines have previously been prepared from *E. coli* by growth on agar surfaces and washing off the live cells, or by growth in liquid media. Use of these live cells as vaccines is believed to carry many risks, eg. infection, severe reaction, possible abortion, etc. Formaldehyde or heat treatments to attenuate the live bacteria may substantially alter the cell constituents which contribute to the development of protective immunity, i.e. the antigenicity may be adversely affected or decreased when cells are treated in this manner.

Among references of interest are the following:
U.S. Pat. No. 3,907,987 issued Sept. 23, 1975;
L. L. Myers et al., Am. J. Vet. Res. (1973) 34:29–33;
F. S. Newman et al., Infect. Immun. (1973) 8:540–543;
L. L. Myers, Am. J. Vet. Res. (1976) 37:831–834
R. A. Wilson et al., Infect. Immun. (1976) 13:92–99.

It would be desirable to prepare *E. coli* vaccines with the full antigenic content associated with live cells yet without the risks associated with active pathogenic bacteria, or with the decreased antigenicity caused by treatment of the whole cells.

Purified antigens such as K99 and polysaccharide K antigens have also been used as vaccines. However, they are believed to be too expensive for use under practical conditions, and their activity is narrow, i.e. purified K99 antigen will induce the formation of only anti-K99 antibodies and the same is true for each individual polysaccharide K antigen. Among the references of interest are the following:
R. E. Isaacson, Infect. Immun. (1977) 15:272–279;
L. L. Myers, Proc. 2nd Int. Symp. Neonatal Diarrhea, Oct. 2–5, 1978. VIDO, Saskatoon.

The vaccine disclosed herein contains K99 antigen as well as polysaccharide K antigens, lipopolysaccharide O antigens, heatstable enterotoxins, all of which may provide protective immunity against colibacillosis; it further contains plasmids, ribosomes, and other cellular organelles, none of which are likely to provide protective immunity.

The advantages of the vaccine according to the invention over vaccines containing whole ETEC cells are the following:

(a) A great deal of extraneous material is removed by the above mentioned processes, including whole cells, large particulate matter, broth by-products, unessential peptides, dextrans, and media components.

(b) The necessary antigenic materials, primarily the K99 antigen, are concentrated, and so can be given in a smaller amount, i.e. a smaller dose to the animal. Packaging and transportation are also facilitated.

(c) There is less alteration to the antigenic components, as they do not have to be formalinized, or otherwise changed.

(d) The disclosed vaccine has less endotoxin.

(e) Because much of the extraneous material is removed, large particles by centrifugation, and small molecules by ultrafiltration, there is less possibility of the animals reacting to foreign materials by anaphylactic shock.

The advantages over vaccines containing only purified K99 antigen are the following:

(a) Many steps of the purification process can be eliminated and therefore the disclosed vaccine can be produced in larger quantities in shorter time which makes its manufacture more economical.

(b) It contains ingredients which will enhance the effectiveness of the vaccine against *E. coli* neonatal diarrhea. These include K99 antigen, polysaccharide K antigens, lipopolysaccharide O antigens, and enterotoxins. If the same vaccines were to be prepared in purified form, each of these 4 components would have to be purified individually.

(c) If an *E. coli* strain producing both labile toxin and stable toxin is used, both toxins are present in the new vaccine.

The invention relates to a method of preventing neonatal diarrhea in calves comprising the step of administering to the pregnant cow prior to parturition a vaccine which induces in the cow effective colostral levels of antibodies against antigens from enterotoxigenic E. coli. Said vaccine comprises an aqueous suspension or solution containing one or more of the following constituents:

K99 Antigens
Polysaccharide K Antigens
Lipopolysaccharide O Antigens
Enterotoxins and lacking whole intact cells, but containing cell fragments and other cellular and culture broth constituents having a molecular weight greater than 1,000, in combination with a suitable adjuvant.

In a preferred embodiment the composition of the vaccine according to this invention contains:
(a) between 0.1 ug/ml, (micrograms per milliliter), and 2.0 mg/ml, (milligrams per milliliter), and more preferably between 0.5 and 500 ug/ml of K99 antigen;
(b) between 20 and 320 nonograms ng/ml and more preferably between 30 and 100 ng/ml of heat-stable enterotoxins; and;
(c) culture broth constituents with a molecular weight greater than 5,000 and more preferably greater than 10,000.

Additionally the vaccine may contain one or more of the following constituents:
plasmids
ribosomes
other cellular organelles Furthermore, the vaccine is combined with an adjuvant selected from the group of Freund's Adjuvant, aluminum hydroxide, aluminum potassium sulfate, or other suitable adjuvants known in the art.

The vaccine according to this invention is preferably administered at least a week prior to parturition and more preferably about 6 weeks and again about 3 weeks prior to parturition. The preferred amount of K99 antigen administered is between 0.5 $\mu$g and 10 mg and more preferably between 2.5 $\mu$g and 2.5 mg per dose.

The vaccine according to this invention induces suitable colostral levels of antibodies in the host. The preferred colostral antibody titers induced in the cow are as follows:
against K99, from $\frac{1}{8}$ to 1/8192
against polysaccharide K, from $\frac{1}{4}$ to 1/128
against lipopolysaccharide O, from 1/32 to 1/1024
Whereby the minimum protective colostral antibody titers are:
against K99, $\frac{1}{8}$
against polysaccharide K, $\frac{1}{8}$
lipopolysaccharide O, $\frac{1}{8}$
Preferred serum antibody titers induced in the cow are as follows:
against K99, from $\frac{1}{8}$ to 1/2048
against polysaccharide K, from $\frac{1}{2}$ to 1/128
against lipopolysaccharide, from 1/16 to 1/128
Whereby the minimum effective serum antibody titers are:
against K99, $\frac{1}{2}$
against polysaccharide K, $\frac{1}{2}$
against lipopolysaccharide O, $\frac{1}{8}$ The invention further relates to a method of making a vaccine useful for preventing neonatal diarrhea comprising of steps of:
(a) Growing several selected enterotoxigenic strains of E. coli in a broth culture medium under aerobic conditions with agitation;
(b) Pooling the different E. coli cultures;
(c) Disrupting the bacteria by input of energy for removal of cell wall polysaccharide outer layers and pili;
(d) Removing intact cells from the disrupted suspension;
(e) Selectively concentrating the subcellular antigens for removal of undesired low molecular weight components and excess water by passing the suspension through an ultrafiltration membrane.

Preferably at least six different enterotoxigenic strains of E. coli are grown and pooled in order to yield a vaccine which contains besides the K99 antigen 6 of more different polysaccharide K antigens and 6 or more different lipopolysaccharide O antigens.

An example of 6 suitable serotypes would be:
(a) 09:K35:K99
(b) 0101:K30:K99
(c) 08:K85:K99
(d) 020:K?:K99
(e) 08:K25:K99
(f) 0101:K28:K99 but any combination of known pathogenic serotypes could be used.

According to the invention the preferred growth conditions for the E. coli strains are:
(a) A broth culture medium which is buffered, preferably with phosphate buffer;
(b) An incubation temperature of 35° to 41° C., preferably of 37° to 38° C. and more preferably of 37.5° C.
(c) An incubation time of 4 to 48 hours, preferably of 8 to 24 hours.

The preferred method of preparing the vaccine from the E. coli culture according to the invention involves:
(a) Disrupting the bacteria by sonication and/or mechanical shearing;
(b) Removing the intact cells from the disrupted suspension by centrifugation, preferably at 35,000 to 50,000 g;
(c) Removing the remaining live cells from suspensions containing the subcellular antigens prior to ultrafiltration, preferably by filtration through an appropriate sterilizing filter;
(d) Using ultrafiltration membranes with an exclusion limit of preferably 1,000 daltons, more preferably of 5,000 daltons and most preferably of 10,000 daltons; and
(e) Treating the selectively concentrated ultrafiltration retentate with preservative and/or stabilizer such as merthiolate or formalin, or, alternatively, lyophilizing the ultrafiltration retentate.

The vaccine according to the invention is prepared by growing selected E. coli strains in a standard broth culture medium under aerobic conditions with agitation. Tryptic soy broth has been found satisfactory but other liquid media may be used such as casamino acid yeast extract, syncase broth as well as other suitable growth media for E. coli known in the art. The bacteria may also be maintained on solid agar media and the cells removed and suspended in broth media.

Aerobic incubation for 4-48 hours at 35°-41° C., preferably for 8-24 hours at 37°-38° C., with vigorous aeration and agitation, provide suitable culture conditions.

One preferred strain of E. coli is B44 (serotype 09:K30;K99:H—) which has been found to give a vaccine having polyvalent antigenicity against K99, K30, and 09 antigens. This strain is being maintained at the Veterinary Infectious Disease Organization, Saskatoon. Other strains are operative and can be selected for use in certain areas where they are responsible for known infections. However, strains which possess the K99 antigen are most effective.

In a preferred embodiment of the present invention several different selected enterotoxigenic strains of K99+ E. coli are grown and subsequently pooled. This procedure ensures that the resulting vaccine contains besides K99 antigen several different polysaccharide K, and lipopolysaccharide O antigens and is, therefore, effective against a wide range of enterotoxigenic E. coli.

The following strains of E. coli were used because they contained antigens to the great majority of enteric bovine pathogens.

(a) 09:K35:K99
(b) 0101:K30:K99
(c) 08:K85:K99
(d) 020:K?:K99
(e) 08:K25:K99
(f) 0101:K28:K99

To release the bacterial cell antigen, the bacteria are disrupted using one or more of the following techniques: mechanical blending, ultrasonication, freezing and thawing and osmotic shock. Sonication and mechanical disruption or a combination thereof have some advantages over other methods in that the surface components (eg. K99 antigen, O and K antigens) are sheared off and minimum lysis of the cells occurs thereby reducing possible death to the animal to be immunized by minimizing the amount of endotoxin released into the medium.

The intensity of disruption will depend on such variables as the type of apparatus used for disruption, volume of sample, and concentration of bacterial cells. For example, using a Brinkman Polytron with a PT10-ST* tip and 100 ml of culture broth, a setting of 5 for 30 minutes is suitable. Prior to disruption, suspension of cells in phophate buffer (0.15 M) with 1 M NaCl (disruption buffer) helps to extract subcellular components, and redisruption in this buffer at least once will increase yields.
* Trade Mark Following disruption, the remaining intact cells can be removed, such as by centrifugation (egs. 35,000× g for 15 minutes in a standard superspeed centrifuge, or 50,000× g in a CEPA model LE continuous centrifuge). The sediment, which generally contains more than 99% of the whole cells, is discarded. The supernatent containing the subcellular antigens can then be sterilized by filtration through appropriate sterilizing filters or any other measure that will remove intact bacteria.

Selective concentration of subcellular antigens is achieved by the use of ultrafiltration membranes supplied by Amicon Corporation. The PM10, DM5, and UM2 membranes (trade mark) are suitable and have significant advantages over other mthods of concentration. Ultrafiltration allows for the selective removal of low molecular weight (<10,000 MW for the PM10, <5,000 MW for the DM5 and <1,000 MW for the UM2 membranes) contaminants that add nothing to the efficacy of the vaccine (egs. intermediate and end products of bacterial metabolism, free amino acids, salts, lipids, dextrans, etc. and some endotoxin). A significant proportion of these materials can be effectively removed while selective concentration of the important active components, which have higher molecular weights, is accomplished in the retentate. This prevents the high concentrations of salts and low-molecular weight, non-volatile compounds that often occurs by lyophilization or evaporation, thus eliminating the need for dialysis or desalting by ion-exchange resins or column chromatography, and decreasing the mass of material which has to be injected thereby increasing the efficacy of the vaccine.

The use of the PM10 membrane (molecular exclusion limit of 10,000 daltons) allows for high flow rates and good removal of the low molecular material. The retentate contains K99 antigen, polysaccharide K antigens, and lipopolysaccharide O antigens, but only 10 to 25% of the heat stable enterotoxins. The use of the DM5 and UM2 membranes (molecular exclusion limits of 5,000 and 1,000 daltons, respectively) allow for the additional recovery of about 75% and 90% of heat-stable enterotoxins, respectively. UM2 membranes have, however, a low filtration rate (10 liters/day) compared to 100 liters/day for DM5 membranes and 200 liters/day for PM10 membranes of the same size.

An example of the conditions for the use of the UM2 (DM5, PM10) membrane would be 5 UM2 membranes in a TC5E module (Amicon, trade mark) with an LP20 A pump (trade mark) operating at a flow rate of 10 liters/minute at a filtration pressure of 40 psi nitrogen. This will give effective ultrafiltration and concentration of the subcellular antigens.

The concentrated material (ultrafiltration retentate) contains the subcellular antigens as well as plasmids, ribosomes and other cellular organelles. The approximate concentrations of some of the active compounds of the retentate are as follows:

K99 Antigen—between 0.1 $\mu$g/ml and 2.0 mg/ml with a preferred amount of between 0.5 and 500 $\mu$g/ml; and Heat-stable enterotoxin—between 20 and 320 ng/ml with a preferred amount of between 30 and 100 ng/ml.

This retentate is combined with effective amounts of preservative and/or stabilizer such as merthiolate or formalin. Alternatively, the retentate can be lyophilized for long term storage.

The vaccine is administered or injected parenterally (eg. subcutaneous, intramuscular, intramammary). Dosage of the vaccine will vary from about 0.1 to 10 ml depending on the degree of concentration of the bacterial antigens. Each dose will usually contain sufficient K99 antigen to give a colostral antibody titer ranging from ⅛ to 1/8192, sufficient polysaccharide K antigen to give a colostral antibody titer ranging from ¼ to 1/128, sufficient lipopolysaccharide O antigen to give a colostral titer ranging from 1/32 to 1/1024, and 20 to 320 ng, preferably 30 to 100 ng of heat-stable enterotoxin(s).

K99 antibody titers were determined by agglutination on slides using as antigen E. coli strain B41 (0101:K99:H-) grown overnight on Minca agar containing 1.0% Isovitalex (BBL)* at 37° C.
*Trade Mark K30 antibody titers were determined by agglutination on slides using a suspension of strain B44 grown on blood agar plates as the antigen. Culturing strain B44 on blood agar enhances development of capsular carbohydrate (K30) which interferes with detectability of K99 and 09 antigens. Hence, strain B44 grown on blood agar failed to agglutinate in K99 or 09 antiserum, but reacted strongly with monospecific K30 antiserum prepared in rabbits according to the method of Edwards et al. (Burgess Publishing Co., Minneapolis, 1972).

09 antibody titers were also determined by agglutination on slides using a suspension of B44 grown on blood agar and autoclaved as the antigen. Autoclaving destroys the K antigens, so the suspension of B44 reacted strongly with 09, but not with K99 or K30 antiserum.

The vaccine is administered to the pregnant dam at least one week prior to parturition. Preferably a series of 2 doses is given at intervals of 2-3 weeks between doses, eg. for cows, about 3 and 6 weeks before calving.

The ultrafiltration retentate containing effective amounts of preservative and/or stabilizer may be combined with an adjuvant, such as Freund's Incomplete Adjuvant, aluminum hydroxide, aluminum potassium sulfate, alhydrogel or other suitable adjuvants known in the art.

The vaccine is evaluated by vaccinating cows and studying the serologic response and by feeding colostrum from vaccinated cows to calves exposed to infection under controlled conditions in which preferably, newborn calves are challenged orally with viable cells of a selected ETEC strain.

The following example is given in illustration of, but not in limitation of, the present invention.

EXAMPLE

A single colony from a freshly streaked blood agar plate of Strain B44 was grown overnight in TS Broth (Difco)* (300 ml) in a shaking water bath at 37° C. and transferred to 10 liters of TS Broth (Difco) in a 12 liter fermentor. The batch was grown overnight at 37° C. with agitation (400 rpm) and aeration (2-4 liters/minute). After culturing the broth was disrupted as described and the cells were removed in a continuous centrifuge at 50,000×g. The supernatant was selectively concentrated over UM2 membranes and 1 liter of retentate was lyophilized. The lyophilized supernatant was resuspended in sterile phosphate buffered saline and 150 ml was filtered through a 0.45 u millipore filter. Part of the sterile retentate was emulsified with an equal volume of Freund's Incomplete Adjuvant (FICA). Each of 7 cows were vaccinated intramuscularly with 10 ml of retentate with adjuvant. (i.e. 5 ml retentate and 5 ml adjuvant). An additional 1.5 ml of retentate without FICA was injected into the two front quarters of the udder through the teat canal using a 2" teat cannula. Each cow was innoculated twice, approximately three and six weeks before parturition. Ten other cows were left as unvaccinated controls. Following parturition, a sample of colostrum was taken from each cow and antibody titers against K99, K30 and 09 antigens determined. Calves were allowed to nurse their dams and when 12-14 hours old were challenged orally with *E. coli* strain B44 grown on Minca agar containing 1% Isovitalex. The results are shown in Tables 1 and 2.

*Trade Mark

TABLE 1
OCCURENCE OF DIARRHEA AND DEATH IN CALVES FOLLOWING CHALLENGE WITH STRAIN B44

| Group | Proportion Of Calves | |
|---|---|---|
| | Diarrheic | Died |
| Retentate | 2/6 | 1/6 |
| Controls | 9/10 | 9/10 |

TABLE 2

| Vaccine | Cow-Calf Number | Clinical Score[a] | % Change In Weight 24 h Post Challenge | Reciprocal Of Antibody Titer[b] | | |
|---|---|---|---|---|---|---|
| | | | | K99 | K30 | 09 |
| Concentrated | 1-2 | 2 | −1.0 | ND | ND | ND[d] |
| Subcellular | 2-3 | 0 | 0.0 | 256 | 32 | 256 |
| Antigens | 3-22 | 3 | ND | 256 | 16 | 64 |
| (Retentate) | 5-39 | 0 | +3.7 | 512 | 32 | 512 |
| | 6-40 | NC[c] | — | 128 | 8 | 512 |
| | 7-53 | 0 | 0.0 | 64 | 8 | 64 |
| | | | +0.4 ± 2.0 | 215[f] | 16 | 181 |
| Unvaccinated | 1-1 | 3 | −21.4 | ND | ND | ND |
| Controls | 2-13 | 3 | −10.0 | — | —[g] | — |
| | 3-14 | 3 | −23.5 | — | — | undil[h] |
| | 4-30 | 3 | −12.2 | — | — | — |
| | 5-31 | 3 | dead | — | — | — |
| | 6-43 | 3 | −18.8 | — | — | 2 |
| | 7-44 | 3 | −16.0 | — | — | — |
| | 8-45 | 3 | −11.7 | — | — | 4 |
| | 9-48 | 3 | −13.9 | — | — | 2 |
| | 10-52 | 1 | 0.0 | — | — | 16 |
| | | | −14.2 ± 7.0 | — | — | 1.9 |

[a] 0 = no diarrhea, dehydration, or depression; 1 = transient softness of feces or watery diarrhea resulting in a loss of 4% of body weight at challenge (BW); 2 = diarrhea accompanied by a loss of 4-11% BW and depression; 3 = diarrhea accompanied by a loss of > 11% BW and death. Calves were weighed at challenge and 12 h, 1, 2, 3, 5, and 10 days postchallenge.
[b] K99, polysaccharide K30 and lipopolysaccharide 09 antibody titers determined by slide agglutination.
[c] Calf injured at birth, not challenged.
[d] ND, not determined
[e] Mean ± SD
[f] Geometric mean titer
[g] —, negative
[h] undil, undiluted The embodiments of the invention in which an exclusive property or privilege is claimed are defined as follows:

1. A vaccine for promoting in cattle the formation of antibodies against antigens from enterotoxigenic *E. coli* comprising an aqueous suspension or solution containing an effective amount of K99 antigen, polysaccharide K antigens, lipopolysaccharide O antigens, enterotoxins, or combinations of the foregoing constituents, said vaccine lacking whole intact cells, but containing cell fragments and other cellular and culture broth constituents having a molecular weight greater than 1000; said vaccine being prepared by a method comprising:
 (a) growing several selected enterotoxigenic strains of E. coli in a broth culture medium under aerobic conditions, with agitation;
 (b) pooling the E. coli cultures;
 (c) disrupting the bacteria by input of energy for removal of cell wall polysaccharide outer layers and pili;
 (d) removing intact cells from the disrupted suspension; and
 (e) selectively concentrating the subcellular antigens for removal of undesired low molecular weight components and excess water by passing the suspension through an ultrafiltration membrane.

2. A vaccine as in claim 1 wherein the cellular and culture broth constituents have a molecular weight greater than 5,000.

3. A vaccine as in claim 1 wherein the cellular and culture broth constituents have a molecular weight greater than 10,000.

4. A vaccine as in claim 1 wherein the aqueous suspension or solution contains 0.1 μg/ml (micrograms/ml) to 2 mg/ml K99 antigen.

5. A vaccine as in claim 1 wherein the aqueous suspension or solution contains 0.5 to 500 μg/ml K99 antigen.

6. A vaccine as in claim 1 wherein the aqueous suspension or solution contains 20 to 320 ng/ml (nanograms/ml) heat-stable enterotoxins.

7. A vaccine as in claim 1 wherein the aqueous suspension or solution contains 30 to 100 ng/ml heat-stable enterotoxins.

8. A vaccine as in claim 1 wherein the aqueous suspension or solution contains a combination of constituents selected from at least two of the groups consisting of K99 antigen, polysaccharide K antigens, lipopolysaccharide O antigens, and enterotoxins.

9. A vaccine as in claim 8 wherein one of the selected constituents is K99 antigen.

10. A vaccine as in claim 9 wherein said combination is K99 antigen, at least one polysaccharide K antigen, at least one lipopolysaccharide O antigen, and at least one enterotoxin.

11. A vaccine as in claim 1 wherein said polysaccharide K antigens are selected from the group consisting of K25, K28, K30, K35, K85, K?, and mixtures thereof; said lipopolysaccharide O antigens are selected from the group consisting of 08, 09, 020, 0101, and mixtures thereof; and said enterotoxins are heat stable enterotoxins.

12. A method of preventing neonatal diarrhea in calves comprising the step of administering to the pregnant cow prior to parturition a vaccine containing an effective amount of K99 antigen, polysaccharide K antigens, lipopolysaccharide O antigens, enterotoxins, or combinations of the foregoing constituents, said vaccine lacking whole intact cells, but containing cell fragments and other cellular and broth constituents having a molecular weight greater than 1000, in combination with a suitable adjuvant, said effective amount of vaccine inducing in the cow effective colostral levels of antibodies against said antigens from enterotoxigenic E. coli; said vaccine being prepared by a method comprising:
 (a) growing several selected enterotoxigenic strains of E. coli in a broth culture medium under aerobic conditions, with agitation;
 (b) pooling the E. coli cultures;
 (c) disrupting the bacteria by input of energy for removal of cell wall polysaccharide outer layers and pili;
 (d) removing intact cells from the disrupted suspension; and
 (e) selectively concentrating the subcellular antigens for removal of undesired low molecular weight components and excess water by passing the suspension through an ultrafiltration membrane.

13. A method as in claim 12, wherein the vaccine is administered to the cow at least a week prior to parturition.

14. A method as in claim 12, wherein the vaccine is administered to the cow about 6 weeks and again about 3 weeks prior to parturition.

15. A method as in claim 12, wherein the vaccine administered to the cow contains 0.5 μg to 10 mg K99 antigen per dose.

16. A method as in claim 12, wherein the vaccine administered to the cow contains 2.5 μg to 2.5 mg K99 antigen per dose.

17. A method as in claim 12, wherein the effective serum antibody titers induced in the cow are as follows:
 against K99, from ⅛ to 1/2048
 against polysaccharide K, from ½ to 1/128
 against lipopolysaccharide O, from 1/16 to 1/128

18. A method as in claim 12, wherein the minimum serum antibody titers induced in the cow are as follows:
 against K99, ½
 against polysaccharide K, ½
 against lipopolysaccharide O, ⅛

19. A method as in claim 12, wherein the effective colostral antibody titers induced are:
 against K99, from ⅛ to 1/8192
 against polysaccharide K, from ¼ to 1/128
 against lipopolysaccharide O, from 1/32 to 1/1024

20. A method as in claim 12, wherein the minimum colostral antibody titers induced are as follows:
 against K99, ⅛
 against polysaccharide K, ⅛
 against lipopolysaccharide O, ⅛

21. A method as in claim 12, wherein the adjuvant is selected from the group of Freund's Adjuvant, aluminum hydroxide and aluminum potassium sulfate.

* * * * *